United States Patent [19]
Steiner

[11] Patent Number: 5,922,839
[45] Date of Patent: Jul. 13, 1999

[54] METHOD OF TREATING HYPERTENSION USING A COMPOSITION CONTAINING A DRIED ANIMAL STOMACH MUCOSA AND ENDOGENOUS PROTEASE-INHIBITOR PEPTIDES

[76] Inventor: Zoltan W. Steiner, Ungerer Str. 19/I/1O5-2, 80802 Munich, Germany

[21] Appl. No.: 08/845,063

[22] Filed: Apr. 21, 1997

Related U.S. Application Data

[63] Continuation-in-part of application No. 08/523,912, Sep. 6, 1995, Pat. No. 5,688,762

[51] Int. Cl.⁶ ..................................................... A61K 38/00
[52] U.S. Cl. ............................... 530/324; 514/12; 514/21
[58] Field of Search ........................ 514/12, 21; 530/324

[56] References Cited

U.S. PATENT DOCUMENTS

| | | | |
|---|---|---|---|
| 4,368,270 | 1/1983 | Weber et al. | 435/226 |
| 4,478,827 | 10/1984 | Haber et al. | 424/177 |
| 4,526,868 | 7/1985 | Schasuzzaman et al. | 435/226 |
| 5,008,273 | 4/1991 | Schnorrenberg et al. | 514/301 |
| 5,134,123 | 7/1992 | Branca et al. | 514/18 |
| 5,688,762 | 11/1997 | Steiner et al. | 514/2 |

OTHER PUBLICATIONS

Vunkakis et al. 'Structural Changes Associated with the Conversiono F Pepsinogen to Pepsin', Biochimica et Biophysica Acta, vol. 22, pp. 537–543, 1956.

Vunkakis et al. 'Structural Changes Associated with the Conversiono F Pepsinogen to Pepsin', Biochimica et Biophysica Acta, vol. 23, pp. 600–608, 1957.

"Structural Changes Associated with the Conversion of Pepsinogen to Pepsin, I. The N–Terminal Amino Acid Residue and Amino Acid Composition of the Pepsin Inhibitor", Vunakis et al., Biochim. Biophys. Acta, vol. 22, pp. 537–543, 1956.

"Structural Changes Associated with the Conversion of Pepsinogen to Pepsin, II. The N–Terminal Amino Acid Residues of Pepsin and Pepsinogen; The Amino Acid Composition of Pepsinogen", Vunakis et al., Biochim. Biophys. Acta, vol. 23, pp. 600–605, 1957.

*Primary Examiner*—Cecilia J. Tsang
*Assistant Examiner*—Anish Gupta
*Attorney, Agent, or Firm*—Roylance, Abrams, Berdo & Goodman, L.L.P.

[57] ABSTRACT

A process of inhibiting the renin angiotensinogen angiotensin mechanism and treating hypertension includes the step of administering a blood pressure lowering amount of a dried stomach mucosa and acidifying agent.

26 Claims, No Drawings

METHOD OF TREATING HYPERTENSION USING A COMPOSITION CONTAINING A DRIED ANIMAL STOMACH MUCOSA AND ENDOGENOUS PROTEASE-INHIBITOR PEPTIDES

CROSS-REFERENCE TO RELATED APPLICATION

This application is a continuation-in-part application of Ser. No. 08/523,912, filed Sep. 6, 1995, now U.S. Pat. No. 5,688,762, by Zoltan W. Steiner which is hereby incorporated by reference in its entirety.

FIELD OF THE INVENTION

The present invention relates to the pharmaceutical use of dried stomach mucosa and an acidifying agent, which produces the pepsin-inhibitor peptide in situ. The pepsin-inhibitor peptide is able to block the renin-angiotensinogen-angiotensin enzymatic system when administered to mammals, including humans. By inhibiting this enzymatic mechanism the production or generation of Angiotensin II is prevented or diminished, which is manifested physiologically by a decrease of the arterial blood pressure of the mammal. The invention is further directed to a method for preparing the dried stomach mucosa.

BACKGROUND OF THE INVENTION

Enzymes and hormones are biocatalysts which control the metabolic processes of an organism. As catalysts, enzymes and hormones increase the rate of one or more reactions and function as directive agents for these occurring reactions. They are of essential importance for living cells. In the blood circulation, enzymes are only present in very limited amounts. They are stored in specific cells in an inactive, insoluble form, and are activated in accordance with the metabolic needs of the organism. The inactive form of the stored enzymes, referred to as zymogens, are enzyme precursors. The activation reaction may be schematically represented as follows:

INACTIVE ZYMOGEN→ENZYME+INHIBITOR+CLEAVED PEPTIDES.

The best known example for the activation process is the pepsinogen compound which is converted into pepsin. In the same way prorenin is activated into renin, and proinsulin into insulin. The reversal of the activation process of zymogen is the blocking of the active enzyme by an inhibitor. A typical example of this process is the pepsinogen-pepsin relationship where pepsin is produced by the activation of pepsinogen. The inhibition of pepsin by an inhibitor produces an inactive compound. Other examples with the possible reversibility of the reaction are the enzymes cathepsin, renin, papain and others.

The principle of the inhibition of an enzymatic reaction is based upon the ability of many organic compounds to react with the enzyme protein, either reversibly or irreversibly, and thus, preventing a reaction between the enzyme and the substrate. It follows that the cleaved inhibitor produced during the activation of the zymogen when reunited with the active enzyme should result in the original zymogen.

Examples of previous studies relating to the structure of pepsin and pepsinogen as well as pepsin are disclosed in Vunakis et al., "Structural Changes Associated with the Conversion of Pepsinogen to Pepsin", *Biochemica Et Biophysica ACTA*, Vol. 22, pp. 537–43 (1956) and Vunakis et al., "Structural Changes Associated with the Conversion of Pepsinogen to Pepsin", *Biochemica Et Biophysica ACTA*, Vol. 23, pp. 600–5 (1957) which are hereby incorporated by reference.

Numerous chemical compounds have been proposed for blocking the renin angiotensin enzymatic process and thereby controlling or treating hypertension. Examples of related processes are disclosed in U.S. Pat. Nos. 5,008,273 to Schnorrenberg et al.; 4,478,827 to Haber et al.; and 5,134,123 to Branca et al.; which are hereby incorporated by reference.

These processes have met with limited success. Accordingly, there is a continuing need in the art for inhibitor compounds, especially of body own-endogenous origin, controlling the blood pressure mechanism.

SUMMARY OF THE INVENTION

The present invention is directed to endogenous enzyme inhibitors, such as those contained in and isolated from the stomach mucosa, or obtained from pepsinogen. The invention is further directed to a dried stomach mucosa and acidifying agent for producing the pepsin-inhibitor peptide in situ in the stomach of the animal. These inhibitors are administered in a pharmaceutically acceptable form to hypertensive mammals, including humans, to decrease the arterial blood pressure by preventing or diminishing the occurrence or formation of the vasopressor Angiotensin II compound, which is one of the causes of high blood pressure. Accordingly, a primary object of the invention is to provide a method of treating hypertension using a protease inhibitor peptide obtained from the stomach mucosa by administering an effective amount of a composition of a dried stomach mucosa and an acidifying agent or a stomach mucosa extract to a hypertensive patient or animal to control their homeostasis.

Another object of the invention is to provide a dried stable stomach mucosa composition that is effective in treating hypertension.

A further object of the invention is to provide a process for obtaining a hog or chicken stomach extract containing the endogenous pepsin inhibitor peptide, which is capable of reacting with Renin and the ACE-enzyme, to form an inactive prorenin-zymogen and an ACE-zymogen.

Another object of the invention is to provide a process for treating hypertension by administering a dried stomach mucosa and acidifying agent to a patient where a pepsin-inhibiting peptide is produced in situ in animal being treated.

A further object of the invention is to provide a composition for treating hypertension comprising a dried stomach mucosa, an acidifying agent and an animal stomach mucosa extract.

Another object of the invention is to provide a process for treating hypertension comprising administering a composition of a dried stomach mucosa, an acidifying agent, purified pepsinogen and an animal stomach mucosa extract.

The foregoing objects are basically attained by suppressing the formation of Angiotensin II in a mammal, said process comprising the steps of administering an effective amount of a composition comprising a mixture of dried stomach mucosa and an acidifying agent to said mammal to produce in situ a pepsin-inhibitor peptide to inhibit the prorenin-renin-angiotensinogen-angiotensin mechanism in said mammal to suppress the formation of Angiotensin II, wherein said pepsin-inhibitor peptide has 29 amino acid residues and a molecular weight of about 3242.

These objects are further attained by a process of comprising drying said mucosa at a temperature of about 20° C. to about 28° C.

The objects of the invention are also attained by providing a process of preparing a composition for treating hypertension comprising drying an animal stomach mucosa at a temperature of 30° C. or less to obtain a dried mucosa, and mixing said dried mucosa with an acidifying agent.

The objects of the invention are further attained by providing a composition for suppressing the formation of Angiotensin II, where the composition comprises a dried stomach mucosa and an acidifying agent.

Other objects, advantages and salient features of the invention will become apparent from the following detailed description which discloses preferred embodiments of the invention.

DETAILED DESCRIPTION OF THE INVENTION

The homeostasis of normal blood pressure in healthy humans is maintained primarily through a regulating system specific for the organism. This self-regulating system establishes an equilibrium between the renin activity and the plasma hormone, angiotensinogen, in such a manner that the production of Angiotensin II, the octapeptide responsible for the blood pressure increase, is maintained at acceptably low levels. When an abnormality in the relationship between renin and angiotensinogen occurs, hypertension is a direct consequence.

Renin, an acid protease of the kidney-cortex, is released into the blood plasma from special cells as the renin precursor, prorenin, is activated in response to a variety of stimuli. Renin enters the blood stream by the reaction with the angiotensinogen of the plasma, the so-called "natural substrate". Angiotensinogen is a tetradecapeptide chain having the structure Asp-Arg-Val-Tyr-Ile-His-Pro-Phe-His-Leu-Leu-Val-Tyr-Ser. In the subsequent metabolic process of the renin activity, this tetradecapeptide is cleaved to form the decapeptide Angiotensin I, Asp-Arg-Val-Tyr-Ile-His-Pro-Phe-His-Leu and the tetrapeptide, Leu-Val-Tyr-Ser.

In the next metabolic step, the decapeptide Angiotensin I is further cleaved by the dipeptidyl, hydrolase, or dipeptidyl-carboxypeptidase enzyme. This is often referred to as the Angiotensin I converting enzyme (ACE). In this step, Angiotensin I is converted into the vasopressor octapeptide Angiotensin II, and a neutral dipeptide His-Leu. Angiotensin II is further degraded by angiotensinase to the heptapeptide Angiotensin III, Arg-Val-Tyr-Ile-His-Pro-Phe by the removal of the terminal Aspartic acid group. The heptapeptide Angiotensin III has an undefined physiological function, but is believed to be the mediator for the secretion of the adrenal cortical aldosterol. Angiotensin II and Angiotensin III have a very short half-life and are further cleaved into smaller inactive peptides. Angiotensin II, the most potent endogenous hormone isolated to date, is involved in the blood pressure homeostasis, and indirectly, via mediation of aldosterol released by the adrenal gland, in the regulation of sodium excretion in the kidney. In the normal undisturbed metabolic flow from an initial macro-molecule of the angiotensinogen substrate, an alpha 2-globulin with a mw of 60,000, a decapeptide angiotensin I is cleaved, with a mw of 1900, followed by a further cleavage to the octapeptide angiotensin II with a mw of 1500, and finally to the heptapeptide Angiotensin III with a mw of 1360. The scheme of the angiotensinogen-renin metabolic process is: Natural renin substrate→Tetradecapeptide→Decapeptide/Angiotensin I→Octapeptide/Angiotensin II→Heptapeptide/Angiotensin III and Neutral Peptides.

Accompanying the decrease of the molecular weight is a decrease of the negative charges of the amino acid chains. This decrease results in metabolites having fewer negative charges than the original substrate. The metabolic process which generates the vasopressor Angiotensin II can be blocked or inhibited on three sites. First, the generation of Angiotensin II can be inhibited by blocking the activation process of prorenin before the inactive zymogen renin is cleaved into renin. Second, the formation of Angiotensin II can be inhibited by blocking the Leu-Leu position in the tetradecapeptide thereby preventing the formation of the decapeptide Angiotensin I. Third, the formation of Angiotensin II can be inhibited by blocking the activity of the Angiotensin I converting enzyme (ACE) and preventing the formation of Angiotensin II.

A large amount of research has been devoted to the problem of preventing the occurrence of high blood pressure, or alleviating its effects. The research resulted in the discovery of inhibitors able to influence the metabolic process of the renin-angiotensinogen system. Two types of agents that block steps in the generation of Angiotensin II in man have been used, namely, Angiotensin I converting enzyme-inhibitors and Angiotensin I receptor blockers. The third alternative to prevent the activation of prorenin into renin in the glomerular cells was not used.

All these attempts are aimed at blocking the enzyme renin and the ACE-enzyme and thus preventing the reaction between enzyme and substrate. Angiotensin I converting enzyme blockers, such as Teprotide, Captoryl, BRL 36378, Enapryl, etc. block the conversion of the decapeptide, Angiotensin I, into the active Angiotensin II and prevent the degradation of the vasodilating hormone bradykinin. These compounds did not solve the problems of hypertension.

The second group of renin blockers prevents the cleavage of the tetradecapeptide substrate in its Leu-Leu sequence by providing means to inhibit the action of renin upon its natural substrate. This can be achieved by competing with the natural substrate for the active binding site of the substrate. To achieve this aim, compounds of the general formula of: Z-His-Pro-Phe-His-Phe-Phe-X-X-Val-Tyr-Y, with the preferred compound "RIPE"-Pro-His-Pro-Phe-His-Phe-Phe-Val-Tyr/D/-Lis were developed. This substituted D-enantiomorph form is not cleaved by renin. Another group is represented by pepstatin and its derivatives, either of natural or synthetic origin, with the sequences isovaleryl-1 Val-L-Valyl-4 amino-3-hydroxy-6-methylheptanoyl-L-methyl-4 amino-3-hydroxy-6-methyl heptanoic stereoisomers and racemates in substituted alkyl, aryl and cyclo components.

By examining the compounds described, it is apparent that they are all of non-endogenous origin and cannot easily adapt to the complexity of the physiological process occurring in the human organism, especially the complex requirements of the homeostasis control.

Inhibitors derived from the activation of a different zymogen can inhibit the activity of a certain given enzyme. For example, it is apparent that under optimal conditions the pepsin inhibitor compound cleaved from pepsinogen can be reunited with the produced pepsin, resulting in the original pepsinogen-zymogen. There are pronounced similarities between the different acid-proteases (e.g., pepsin, catepsin, renin, proctase, papain), for instance: 1) all have the optimum of activity in ranges of pH 2–4.5, depending on substrate; 2) their activity is inhibited by the activated pentapeptide pepstatin; 3) they all are inhibited by aliphatic diazo-compounds, e.g., diazo-acetyl-D-L-norleucinmethylester; and 4) they are not inhibited by the inhibitors EDTA, diisopropyl-phosphofluoride or p-hydromercurobenzoate. One of the important findings of this invention is that the transfer of an acidic protease inhibitor to another acidic protease can take place, transforming it into an inactive zymogen. For instance, the transfer of the pepsin blocking inhibitor can block the activity of the renin enzyme.

The present invention is directed to the discovery that by using the natural regulating mechanism of homeostasis produced by the organism's metabolism, a blood pressure equilibrium can be achieved by administering compounds of endogenous origin, i.e., compounds existing in healthy animals. This substitutional therapy is achieved by administering an amount of an endogenous enzyme inhibitor to a mammal, including humans, namely the pepsin-inhibitor peptide, to decrease the blood pressure of the subject and prevent or treat hypertension.

The invention is further directed to an improved process for preparing an animal stomach mucosa extract and a composition of a dried stomach mucosa and an acidifying agent having pepsin and renin inhibiting activity.

The present invention is primarily directed to a method of suppressing the formation of Angiotensin II and treating hypertension in an animal. The method includes the step of administering an effective amount of a pepsin-inhibitor peptide obtained from pepsinogen or dried stomach mucosa composition or mixtures thereof to reduce the blood pressure of an animal in need thereof. The peptide-containing extract or composition can be in the form of tablets, coated tablets, capsules, granules, suppositories or solutions. The extract can be administered orally, subcutaneously or parenterally according to standard procedures. The dried stomach mucosa composition is preferably administered orally.

The inhibitor peptide-containing extract is obtained from a number of different sources. In preferred embodiments, the inhibitor peptide-containing extract and inhibitor peptide producing composition is obtained from hog stomach mucosa. In alternative embodiments, the peptide-containing extract is obtained from other animal stomach mucosa including, for example, fowls, such as chickens, turkey or ostrich, and mammals such as cows, dogs, cats and rodents. In still further embodiments, the inhibitor-peptide containing extract or inhibitor-peptide producing composition can be obtained by esterification, acetylation, condensation and polymerization reactions of the peptides in the extract.

One aspect of the invention is directed to the discovery that a composition of a dried stomach mucosa and an acidifying agent when administered orally to a patient suffering from hypertension produces a drop in blood pressure. It is believed that the dried stomach mucosa in the presence of an acidifying agent produces the pepsin-inhibitor peptide in situ in the stomach of the animal. The reaction can be summarized as follows:

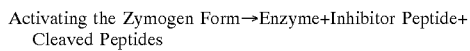
Activating the Zymogen Form→Enzyme+Inhibitor Peptide+ Cleaved Peptides The stomach mucosa is preferably, dried under mild conditions to avoid changing the composition of the naturally occurring compounds of the live gastric cell and to maintain enzymes contained therein in an active form. The dried stomach mucosa is generally prepared by obtaining the stomach mucosa from a recently slaughtered animal, such as a hog. The stomach mucosa is cleaned by washing with water to remove solid impurities. The excess wash water is removed to obtain a clean stomach mucosa. The stomach can be washed in lukewarm water. A 1% second washing step can be performed using for example, a by weight aqueous potassium sorbate solution or other cleaning solution that does not adversely affect the stomach mucosa.

In preferred embodiments of the invention the cleaned stomach mucosa is sterilized to kill any remaining harmful organisms adhering to the surface of the mucosa. Preferably, the stomach mucosa is sterilized by irradiating with ultraviolet light. The intensity and wavelength of the ultraviolet light are set to known standards for sterilization using commercially available equipment. In further embodiments, other known sterilizing techniques can be used which do not destroy the enzymes in the stomach mucosa.

The cleaned stomach mucosa is then passed through a meat mincing, grinding or chopping machine to produce a paste. The resulting paste is then dried at a temperature of about 30° C. or less and preferably, a temperature of about 20° C. to about 28° C. to produce dry granular lumps. Preferably, the minced stomach mucosa is dried to a sufficiently low moisture content to produce free flowing granular material. The minced stomach mucosa can be dried at atmospheric pressure or under vacuum using standard drying equipment. A suitable drying apparatus is, for example, a drum drier, sheet drier or sieve as known in the art.

In a preferred form of the invention, the cleaned and minced stomach mucosa is mixed with an inert filler material prior to drying to increase the volume of the paste, increase the drying efficiency, reduce the overall initial moisture level, and to reduce the stickiness of the paste. The filler material is a fine granular material that is thoroughly mixed with the minced stomach mucosa to form a paste. The filler material is preferably a material that improves the drying efficiency and the granulating properties of the resulting dried material.

The filler material is preferably mixed with the minced stomach mucosa in the amount of about 10% to about 30% by weight based on the total weight of the final composition. Suitable filler materials include, for example, wheat flour, such as samolina flour, lactose, starch, such as wheat, potato or corn starch, sucrose, silica gel, talc, stearic acid salts and mixtures thereof.

The dried stomach mucosa is then mixed in a suitable mixing or kneading machine with a pharmaceutically acceptable acidifying agent in an amount to produce a pH of about 1.0 to about 4.5 in a 0.9% saline solution or in situ in the animal being treated. The acidifying agent is preferably included to produce a pH in the stomach of the animal being treated of about 1.0 to 4.5 to convert the pepsinogen in situ to pepsin and the pepsin inhibiting peptide. The pepsin inhibiting peptide is then available for treating hypertension. Suitable acidifying agents include, for example, betain hydrochloride, fumaric acid, tartaric acid, sorbic acid, dihydrogen sodium phosphate, and mixtures thereof. It is to recognize that other acidifying agents capable of producing the necessary pH can be used.

The resulting composition is a dry granular material containing whole dried stomach mucosa, an optional inert filler and an acidifying agent. The dry composition is stable at room temperature for extended periods of time. The dry material is preferably granulated in a ball-mill or other granulating or milling device to reduce the particle size for ease of handling and for reaction with the acidifying agent. Preferably, the dried composition is prepared for oral administration in the form of tablets, coated tablets, capsules, powder and the like.

The composition containing the dried stomach mucosa, acidifying agent and option filler is preferably administered orally in the amount of about 1,000 mg to 3,000 mg per dose. The dosage is preferably given three times daily. Alternatively, the composition is administered at a daily dosage of about 50 mg per kg of body weight which corresponds to a daily dosage of about 1,000 mg to 9,000 mg.

When administered orally to an animal, the acidifying agent reacts with the stomach mucosa to produce the pepsin inhibitor peptide having 29 amino acid residues and a molecular weight of about 3242. The composition is an effective vasodepressor composition from naturally occurring animal organ. The method preserves the properties of the naturally occurring cells and creates the proper conditions for the activating process of pepsinogen conversion to produce the protease inhibitor peptide.

In embodiments of the invention, the composition for treating hypertension includes the dried animal stomach mucosa, an acidifying agent and the animal stomach mucosa extract prepared as discussed hereinafter in greater detail. In still further embodiments, the composition can contain purified pepsinogen or the pepsin inhibitor peptide in combination with the dried animal stomach mucosa, acidifying agent and animal stomach mucosa extract.

The protease inhibiting peptide-containing extract of this invention contains the pepsin-inhibitor peptide, namely the pepsin and renin inhibitor peptide. The composition of the dried stomach mucosa and acidifying agent produces the protease inhibiting peptide in situ. The extract and the dried composition are found to inhibit the activity of pepsin and also inhibit the activity of renin thereby inhibiting the renin-angiotensinogen-angiotensin metabolism. This inhibiting effect of the extract suppresses the formation of Angiotensin II and produces a blood pressure lowering effect in humans and other mammals. The blood pressure lowering effect is obtained by blocking the renin angiotensin and Angiotensin I converting enzyme system. The invention is also directed to the discovery that the pepsin inhibitor has an inhibiting effect on pepsin and also renin, thereby causing a blood pressure lowering effect in animals.

The stomach mucosa extract and the pepsin inhibitor peptide affect the renal cells where the extract blocks or inhibits the activation of zymogen prorenin into renin. The stomach mucosa extract also affects the renin activity upon the natural substrate in the circulating plasma by first blocking the Leu-Leu site of the tetradecapeptide, thereby blocking the cleavage of the Angiotensin I decapeptide. The stomach mucosa extract further inhibits the activity of the Angiotensin I Converting Enzyme (ACE), blocking the formation of Angiotensin II from Angiotensin I.

In one embodiment of the invention, the inhibitor peptide-containing extract is obtained from animal stomach mucosa and, in particular, hog stomach mucosa. The extract is essentially obtained by forming a paste of the minced mucosa, by adding an acidified solvent to precipitate the proteins and dissolve the low molecular weight peptide inhibitor. Generally, the solvent is ethanol acidified to a pH of about 2–5.5. The preferred acidifying acid is hydrochloric acid. The solution is formed from an organic solvent, such as ethanol, or other alcohol, or an aqueous solvent, such as a saline solution. (0.9% sodium chloride in distilled water.)

The acidified supernatant is filtered to recover the filtrate, which then is evaporated to dryness, or to a viscous fluid, and then solubilized in ethanol. The residue is discarded and the filtered solution concentrated by evaporating the solvent under a vacuum to obtain the inhibitor peptide containing extract.

The extraction process is preferably carried out under mild conditions, at a temperature below about 30° C., preferably below 37° C., at a pH of about 2–5.5, and with a salt concentration of about 0–9% sodium chloride. The processing conditions are similar to those found in the body. This produces a pepsin inhibitor peptide extract that is compatible with and stable in the body. The extract can be purified by fractionating by the tungstate precipitation method as known by those skilled in the art.

The obtained stomach mucosa extract has a molecular weight of 10,754 and an average number of 101 amino acid residues per mole as follows:

| Amino Acid | Number of Residues by Chromatography (nearest integer) |
|---|---|
| Aspartic acid | 7 |
| Glutamic acid | 10 |
| Glycine | 9 |
| Alanine | 9 |
| Valine | 8 |
| Leucine + Isoleu | 15 |
| Serine | 6 |
| Threonine | 5 |
| Proline | 12 |
| Phenylalanine | 2 |
| Tyrosine | 1 |
| Lysine | 7 |
| Arginine | 5 |
| Methionine | 2 |
| Histidine | 3 |
| Total amino acid residues per mol | 101 |

The stomach mucosa extract obtained by the processes of the invention is stable for extended periods of time when stored at room temperature of about 25° C. Sterilization of the extract at 120° C. has also been shown to have little or no effect on the activity of the extract.

In vivo test results have shown the efficacy of the stomach mucosa extract in lowering blood pressure in a frog's heart, small intestines, dogs (awake and under anesthesia), dogs in long term feeding tests, genetically hypertensive rats, and human volunteer patients. No adverse, toxic or immunological side effects have been observed.

Pure pepsin inhibitor has 29 amino acid residues and a molecular weight of 3242 as determined in Vunakis et al., "Structural Changes Associated with the Conversion of Pepsinogen to Pepsin", Biochemica Et Biophysica ACTA, Vol. 22, pp. 537 (1956). The amino acid residue content of the pepsin inhibitor is as follows.

| Amino Acid | Number of Residues by Chromatography (Nearest Integer) |
|---|---|
| Aspartic acid | 4 |
| Glutamic acid | 2 |
| Glycine | 1 |
| Alanine | 2 |
| Valine Leucine) | 2 |
| Isoleucine | 5 |
| Serine | 2 |
| Threonine | 1 |
| Proline | 3 |
| Phenylalanine | 1 |
| Tyrosine | 1 |
| Lysine | 4 |

| Amino Acid | Number of Residues by Chromatography (Nearest Integer) |
|---|---|
| Arginine | 1 |
| | 29 |

The pure pepsin inhibitor has also been found to have a blood pressure lowering effect in animals and to suppress the formation of Angiotensin II by blocking or inhibiting the renin-angiotensinogen-angiotensin enzymatic system. In embodiments of the invention, a mixture of the inhibitor peptide containing extract and pure pepsin peptide is administered to the animal. The preferred mixture is a 1:1 mixture by weight.

The inhibitor peptide-containing extract is found to have a blood pressure lowering effect when administered to an animal. The extract inhibits the activity of pepsin and also of renin in complex systems of renin-angiotensinogen.

The dosage of the pepsin-containing extract can vary, depending on the animal and method of administration as recognized by one skilled in the art. By way of experimental data, it has been found that daily oral administration in the range of about 12–12.5 mg/kg of body weight is effective in providing a blood pressure lowering effect. The calculated amount is based on a composition having a ratio of 1:10 of the pepsin-inhibitor containing extract to a pharmaceutically acceptable carrier. Parenteral administration on a daily basis in the amount of about 5 mg/kg of body weight is effective where the amount is a diluted composition of the pepsin-inhibitor containing extract and pharmaceutically acceptable carrier.

The following non-limiting examples depict preferred embodiments of the invention.

EXAMPLE 1

This example produces a dried stomach mucosa. 1,000 g fresh stomach mucosa from a recently slaughtered hog was cleaned with lukewarm water to remove solid impurities. The mucosa was then cleaned mechanically to remove adhered slime and mucus and then washed in a water solution containing 1% potassium sorbate. The mucosa was then soaked in the potassium sorbate solution for 30 minutes. The excess of the potassium sorbate solution is drained from the stomach mucosas by placing the mucosa on an inclined table or strainer. The washed stomach mucosas is then passed through a tunnel irradiated with UV-rays to sterilize the mucosa. The material was then minced using a mincing machine to produce a paste. The resulting homogenous paste was mixed with 20 weight percent of semolina wheat flour in a kneading machine. The resulting paste was dissicated in food drying device. In the drying process the temperature of the treated mucosa tissue material was held at 30° C. or less. The consistency of the resulting dried tissue material was in the form of dry free flowing granules.

This dried material was introduced in a ball-mill and crushed to a uniform powder and passed through a sieve to remove any large or agglomerated lumps. The sieved powder material was mixed with the following activating chemical compounds and inactive ingredients:

Activating Chemicals:

Betain hydrochloride 10 weight %

Sorbic Acid 0.05 weight %

Inert Ingredients:

Silica gel 0.1 weight %

Other additives: 0.068 weight %

The percentages are based on the total weight of the final composition with the remainder being the dried stomach mucosa.

This composition was filled in pharmaceutically used gelatin capsules containing each 1,000 mg active tissue, and activating chemicals, and 168 mg inactive additives.

EXAMPLE 2

1,000 g fresh stomach mucosa from recently slaughtered hogs was cleaned with lukewarm water to remove solid impurities. The mucosa was then cleaned mechanically to remove the adhered slime and mucus. The cleaned mucosa was placed in a water solution containing 1% potassium sorbate for about 30 minutes. The excess sorbate solution was drained from the stomach mucosa by placing the mucosa on an inclined table. The mucosa was then minced using a meat mincing machine to produce paste. The resulting homogenous paste was lyophilized using a commercially available lyophilizing device. The resulting dry fibrous material was introduced in a ball mill and milled to a homogenous powder. The sieved powder material was mixed with betain hydrochloride and potassium dihydrogen phosphate as an activating compound and silica gel as an inert filler to obtain a uniform fine grained powder mass. The resulting powder contained 100 g of betain hydrochloride and 2.0 g of potassium dihydroden phosphate and 0.1% of weight silica gel. The composition was placed in pharmaceutical gelatin capsules each containing 1,000 mg active mucosa tissue, activating chemicals and inert ingredients.

EXAMPLE 3

1,000 g rennet calf stomach from recently slaughtered calf not older than 4–5 months was cleaned twice with cold tap water to remove all solid impurities. The stomach was placed in a water solution containing 1% potassium sorbate for 30 minutes. The excess of sorbate solution was drained from the tissue material by placing the material on an inclined table. This material was minced in a meat grinder to obtain a homogenous tissue paste. The paste was dried in thin layers in a vacuum dryer at a temperature of 28° C. or less, to obtain lumps of a granular material. This material was mixed with samolina wheat flour, betain hydrochloride and silica gel in a ball-mill and milled therein to a uniform fine powder. The powder was passed through a sieve to remove any remaining large particles. The sieved, uniform powder was passed through a tunnel irradiated with UV-rays and placed in pharmaceutical gelatin capsules.

Composition of the end product:

Dried organ tissue material: . . . 75%

Samolina Wheat Flour . . . 16%

Betain hydrochloride . . . 8%

Silica gel . . . 1%

Each capsule containing 1250 mg of this composition.

EXAMPLE 4

1,000 g fresh stomach mucosa of turkey was cleaned to remove impurities and washed twice with lukewarm water. The mucosa was immersed in a 2% aqueous solution of potassium sorbate. The excess sorbate solution drained and the mucosa passed through a meat mincer to a form homogenous paste.

To this paste 100 g samolina wheat flour was added and the mixture introduced in a meat kneading machine and kneaded to a homogenous paste. The paste was then spread in a thin layer of not more than 1–1.5 cm in height on broad mesh sieves and placed in a vacuum dryer. The vacuum drier utilized was a commercially available drier used in the pharmaceutical industry. The drying temperature did not exceed 28° C. The granular dried lumps are mixed with the betain hydrochloride, sorbic acid and sodium dihydrogenphosphate as activating and silica gel as the inert filler. This mixture was milled in a ball mill to a fine powder, irradiated with UV-rays and filled in pharmaceutical gelatin capsules, each containing 1250 mgs of the dried composition.

EXAMPLE 5

1,000 g fresh stomach mucosa from a recently slaughtered hog was cleaned with lukewarm water to remove solid impurities. The mucosa is then minced using a mincing machine. The resulting paste was mixed with 1,000 ml of 95 Vol % ethanol containing hydrochloric acid to pH 5. The mixture was mixed homogeneously and incubated at 30° C. for 10 minutes, then centrifuged at 1,200 r/min. The supernatant liquid was collected. The remaining solids were extracted twice with the ethanol solvent to improve the recovery yield. The collected liquids were mixed, and the alcohol solvent evaporated under vacuum at 100 mmHg, and concentrated to a volume of 300 ml to produce a viscous liquid. 1,000 ml of 95 Vol % ethanol was added to the viscous liquid, and the pH adjusted to pH 5 with hydrochloric acid, while stirring continuously to precipitate the pepsin proteins. The precipitated pepsin proteins were separated by filtration, discarded, and the supernatant liquid evaporated to dryness. The resulting sticky residue was dissolved in 300 ml of 95 Vol % ethanol. To this solution, active charcoal was added, and the resulting solution filtered and liberated from alcohol to a dry consistency. The residue was twice extracted with isobutyl alcohol to remove lipoids and fats. The alcohol solvent was removed by evaporation and the resulting extract was dissolved in 100 ml physiological grade 0.9% sodium chloride saline. The inhibitory activity of the solution is related to the initial weight of the stomach mucosa and is 1:10. (One gram of extract from log of mucosa.)

The amino acid content and molecular weight of the pepsin inhibitor peptide and the mucosa extract are as discussed above.

EXAMPLE 6

1,000 g fresh hog stomach mucosa from a recently slaughtered hog was cleaned with lukewarm water to remove solid impurities. The mucosa was minced using a mincing machine. The resulting paste was mixed with 1,000 ml of 0.9% sodium chloride solution, adjusted to pH 6.0 using hydrochloric acid, and incubated at 30° C. for three hours. To this paste, minced wood shavings, minced straw and polyethylene granules were added to form a semi-dry mixture. This mixture was placed in linen bags and squeezed in a filter press to recover the extract. The extract was mixed with a 72% solution of ammonium sulfate by adding slowly until no more precipitation occurs. After sedimentation of the precipitate, the mixture is filtered. The filtrate is deionized. The salt free solution is concentrated in vacuo to a viscous fluid. A 0.9% sodium chloride solution was added to the viscous fluid to make 100 ml. This solution, with a standard inhibitory activity of 1:10 in relation to the initial stomach mucosa weight, shows identical characteristics as the extract described in Example 1.

EXAMPLE 7

The extracted fluid obtained by the pressing process of Example 6 is adjusted to pH 5.5 with hydrochloric acid and incubated at 30° C. for three hours. The solution is then passed through a Sephadex affinity chromatography column.

EXAMPLE 8

1 g of commercial grade Pepsinogen was dissolved in 10 ml distilled water and acidified with hydrochloric acid at pH 2.5 at 15° C. for a few minutes. The solution was then made alkaline with 20% sodium hydroxide solution to pH 8.0 and allowed to stand for 15 minutes. The resulting pepsin/pepsin inhibitor-peptide complex was acidified to pH 5.5. In this solution, pepsin was precipitated with 95 Vol % ethanol, and the mixture put aside for sedimentation. After the separation of the pepsin precipitate by filtration, the resulting solution was passed through an anionic resin column. The acidic and neutral fractions were discarded. The basic peptides adhering to the column were eluted with 7.2% hydrochloric acid, and the eluate concentrated in vacuo. The inhibitory activity of the peptide was tested by Radioimmunoassay.

IN VIVO TESTS

EXAMPLE 9

| | Initial | Minutes After Administration | | | | |
|---|---|---|---|---|---|---|
| | MAP | 5 | 10 | 1 | 4 | 2 |
| The effect of hog stomach extract 1:10/of exam.1/upon main arterial blood pressure/MAP/ Applied: 2 ml | 173 | 99 | 149 | 150 | 146 | 1 |
| The effect of pepsin inhibitor peptide/ Ex. 8/upon main art. blood pressure Applied: 1.5 ml | 170 | 100 | 136 | 155 | 170 | 1 |
| The effect of stomach mucosa extract upon MAP in essential hypertensive volunteers Total administered Hog stomach mucosa extract: | 210 | After 3 days 180 mmHg After 7 days 170 mmHg After 4 wks. 160–162 mmHg  250 mg/kg body weight | | | | |

The administration of dried hog stomach mucosa and acidifying agent composition to spontaneous hypertensive rats produced a statistically significant (p 0.05) reduction in blood pressure on day 7, 10, 14 and 17 when compared to pretreatment on Day zero (0).

EXAMPLE 10

In this example, the blood pressure lowering effects of the extract obtained from Example 1 are analyzed using genetically hypertensive rats. A saline solution containing 10% of the extract (1:10) was prepared. A 2 ml dose per kg of body weight was administered intravenously to each rat. The rats had an average initial blood pressure of 185 mmHg before administration of the extract-containing solution. After five minutes, the average blood pressure was 105 mmHg, and after four hours the blood pressure was 160 mmHg.

EXAMPLE 11

A group of human volunteer patients suffering from hypertension was used in this study. A saline solution containing 10% of the extract of Example 1 (1:10) was prepared. The solution was administered orally in the amount of 250 mg/kg of body weight over a period of seven days. The treatment scheme was as follows.

| Day | Dosage (mg/kg body weight) |
| --- | --- |
| 1 | 12.5 |
| 2 | 25.0 |
| 3 | 50.0 |
| 4 | 75.0 |
| 5 | 50.0 |
| 6 | 25.0 |
| 7 | 12.5 |

The patients showed an average blood pressure reduction the amount of 30–50 mmHg over this seven day period.

While advantageous embodiments have been chosen to describe the invention, it will be understood by those skilled in the art that various changes and modifications can be made therein without departing from the scope of the invention as defined in the appended claims.

What is claimed is:

1. A process for suppressing the formation of Angiotensin II in a mammal, said process comprising the steps of
administering an effective amount of a composition comprising a mixture of dried stomach mucosa and an acidifying agent to said mammal to produce in situ a pepsin-inhibitor peptide to inhibit the prorenin-renin-angiotensinogen-angiotensin mechanism in said mammal to suppress the formation of Angiotensin II, wherein said pepsin-inhibitor peptide has 29 amino acid residues and a molecular weight of about 3242.

2. The process of claim 1, wherein said acidifying agent is selected from the group consisting of betain hydrochloride, sorbic acid, tartaric acid, fumaric acid, dihydrogen sodium phosphate and mixtures thereof.

3. The process of claim 1, wherein said composition further comprises about 10 to 30% by weight of an inert particulate filler selected from the group consisting wheat flour, silica gel, starch, lactose, sucrose, talc, stearic acid salts and mixtures thereof.

4. The process of claim 1, wherein said composition further comprises a component selected from the group consisting of a pepsin-inhibitor peptide, purified pepsinogen, an animal stomach mucosa extract and mixtures thereof.

5. The process of claim 1, wherein said acidifying agent is present in an amount to produce when in solution of pH of about 1.0 to 4.0.

6. The process of claim 1, comprising administering said composition at a daily rate of 1000 to 9,000 mg.

7. The process of claim 1, comprising administering said composition at a daily rate of about 50 mg per kg of body weight.

8. The process of claim 1, wherein said dried stomach mucosa is sterilized by subjecting said stomach mucosa to ultraviolet light.

9. The process of claim 1, wherein said dried stomach mucosa is prepared by drying a minced stomach mucosa at a temperature of about 30° C. or less.

10. The process of claim 1, wherein said dried stomach mucosa is prepared by lyophilizing a stomach mucosa.

11. The process of claim 1, wherein said dried stomach mucosa is obtained from the group consisting of hog, cow, chicken, turkey, rodents, dog, cat and mixtures thereof.

12. The process of claim 1, comprising drying said mucosa at a temperature of about 20° C. to about 28° C.

13. A process of preparing a composition for treating hypertension comprising the steps of
rinsing fresh animal stomach mucosa to remove excess material and mincing said stomach mucosa to form a paste;
mixing said paste with a substantially inert filler material selected from the group consisting of wheat flour, lactose, starch, sucrose, silica gel, talc, and stearic acid salts in an amount of about 25% to about 30% by weight based on the total weight of said composition;
drying said animal stomach mucosa paste at a temperature of 30° C. or less to obtain a dried mucosa, and
mixing said dried mucosa paste with an acidifying agent to produce a substantially dry composition having hypertension suppressing activity.

14. The process of claim 13, comprising drying said stomach mucosa at a temperature of about 20° C. to about 28° C.

15. A process of preparing a composition for treating hypertension comprising drying an animal stomach mucosa at a temperature of 30° C. or less to obtain a dried mucosa,
mixing said dried mucosa with an acidifying agent to form a dried mucosa mixture, and
admixing a said dried mucosa mixture with at least one selected from the group consisting of purified pepsinogen, a pepsin-inhibitor peptide, an animal stomach mucosa extract and mixtures thereof.

16. The process of claim 13, comprising
drying said stomach mucosa by lyophilization.

17. The process of claim 13, comprising admixing said dried mucosa with a sufficient amount of an acidifying agent to produce a solution having a pH of about 1.0 to about 4.5.

18. A process of preparing a composition for treating hypertension comprising the steps of
drying an animal stomach mucosa at a temperature of 30° C. or less to obtain a dried mucosa, and
mixing said dried mucosa with an acidifying agent selected from the group consisting of betain hydrochloride, sorbic acid, tartaric acid, fumaric acid, dihydrogen sodium phosphate and mixtures thereof to produce a composition having hypertension suppressing activity.

19. A process of preparing a composition for treating hypertension comprising the steps of
drying an animal stomach mucosa at a temperature of 30° C. or less to obtain a dried mucosa,
sterilizing said mucosa by subjecting said mucosa to ultraviolet light, and
mixing said dried mucosa with an acidifying agent to produce a composition having hypertension suppressing activity.

20. A pharmaceutical composition for suppressing the formation of Angiotensin II comprising:
a dried stomach mucosa, and an acidifying agent in an amount to produce a pH sufficient to produce a pepsin-inhibitor peptide in situ.

21. The composition of claim 20, further comprising a purified pepsinogen, a pepsin-inhibitor peptide animal stomach mucosa extract and mixtures thereof.

22. The composition of claim 20, further comprising about 10% to about 30% by weight of an inert filler selected from the group consisting of wheat flour, silica gel, starch, lactose, sucrose, talc, stearic acid salts and mixtures thereof.

23. The composition of claim 20, wherein said acidifying agent is included in an amount to produce a solution of pH of about 1.0 to about 4.5, wherein said acidifying agent is selected from the group consisting of betain hydrochloride, sorbic acid, tartaric acid, fumaric acid, dihydrogen sodium phosphate and mixtures thereof.

24. The composition of claim 23, wherein said dried stomach mucosa is selected from the group consisting of hog, cow, chicken, turkey, rodents, dog, cat and mixtures thereof.

25. The process of claim 1, further comprising the step of dispersing about 10% by weight of said composition of dried stomach mucosa and acidifying acid to form an aqueous dispersion and thereafter administering said dispersion to said mammal.

26. The process of claim 13, further comprising the step of dispersing about 10% by weight said composition of dried animal stomach mucosa and acidifying agent to form an aqueous dispersion.

* * * * *